(12) United States Patent
Dardenne et al.

(10) Patent No.: US 8,731,253 B2
(45) Date of Patent: May 20, 2014

(54) HELP SYSTEM FOR IMPLANTING A HIP PROSTHESIS ON AN INDIVIDUAL

(75) Inventors: Guillaume Dardenne, Brest (FR); Eric Stindel, Locmaria Plouzane (FR); Chafiaa Hamitouche, Plouzane (FR); Christian Roux, Saint-Renan (FR)

(73) Assignee: Universite de Bretagne Occidentale, Brest Cedex (FR)

( * ) Notice: Subject to any disclaimer, the term of this patent is extended or adjusted under 35 U.S.C. 154(b) by 1039 days.

(21) Appl. No.: 12/488,001

(22) Filed: Jun. 19, 2009

(65) Prior Publication Data

US 2009/0316967 A1 Dec. 24, 2009

Related U.S. Application Data

(60) Provisional application No. 61/074,328, filed on Jun. 20, 2008.

(51) Int. Cl.
*G06K 9/00* (2006.01)
(52) U.S. Cl.
USPC .......................................................... 382/128
(58) Field of Classification Search
None
See application file for complete search history.

(56) References Cited

U.S. PATENT DOCUMENTS

| | | | |
|---|---|---|---|
| 2,703,080 A * | 3/1955 | Sanders ........................... 601/24 |
| 6,205,411 B1 * | 3/2001 | DiGioia et al. .................. 703/11 |
| 6,514,219 B1 * | 2/2003 | Guimond et al. ............. 600/595 |
| 7,302,288 B1 * | 11/2007 | Schellenberg ................ 600/427 |
| 7,877,131 B2 * | 1/2011 | Jansen et al. .................. 600/424 |
| 8,007,448 B2 * | 8/2011 | Moctezuma de La Barrera .......................... 600/587 |
| 2003/0153829 A1 | 8/2003 | Sarin et al. |
| 2004/0087852 A1 * | 5/2004 | Chen et al. .................... 600/407 |
| 2005/0203536 A1 | 9/2005 | Laffargue et al. |
| 2006/0100504 A1 * | 5/2006 | Jansen et al. .................. 600/424 |

FOREIGN PATENT DOCUMENTS

| | | |
|---|---|---|
| FR | 2865928 A1 | 8/2005 |
| WO | 2004030559 A1 | 4/2004 |
| WO | 2007147235 A1 | 12/2007 |
| WO | 2009/071503 A1 | 6/2009 |

OTHER PUBLICATIONS

A mechanical instrument for 3D ultrasound probe calibration Gee et al, pp. 505-518 Apr. 1, 2005.*
French Search Report for foreign Application No. FR0854114, dated Feb. 27, 2009.

* cited by examiner

*Primary Examiner* — Nancy Bitar
(74) *Attorney, Agent, or Firm* — David D. Brush; Westman, Champlin & Koehler, P.A.

(57) ABSTRACT

A system and method are provided for helping implant a hip prosthesis in an individual, which includes an acetabulum intended to be placed in the hip bone of the patient and a femoral part intended to be integrally connected to the femur of the individual. The method includes: obtaining, before the operation, images issued by a device that images a human body and locates a position of images in space. The images are taken in at least three reference positions: standing; recumbent; and sitting. Before the operation, the method determines a pelvis version of the individual in different positions by analyzing the images. During the operation, the method measures a position of the acetabulum with relation to the pelvis of the individual, and simultaneously restores information representative of prosthetic mobility of the hip with relation to each of the reference positions, for a current position of the acetabulum.

12 Claims, 8 Drawing Sheets

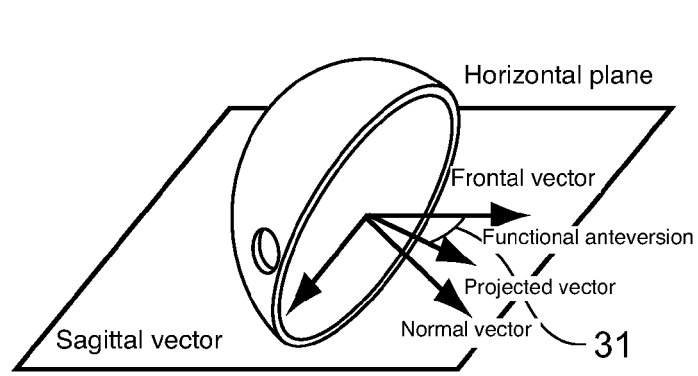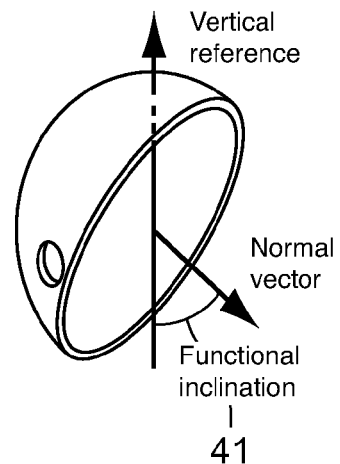
Fig. 3               Fig. 4
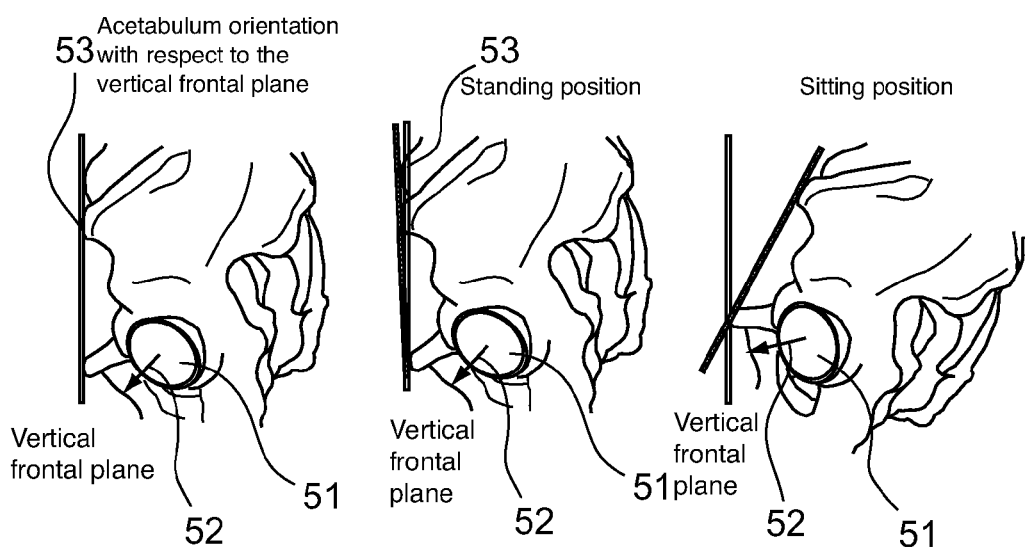
Fig. 5A      Fig. 5B      Fig. 5C

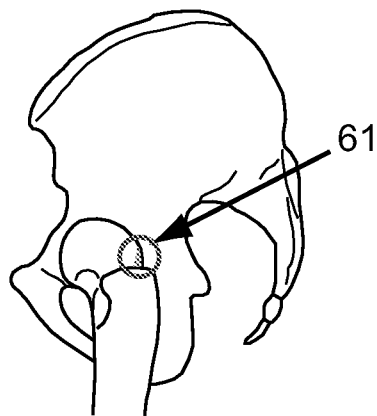
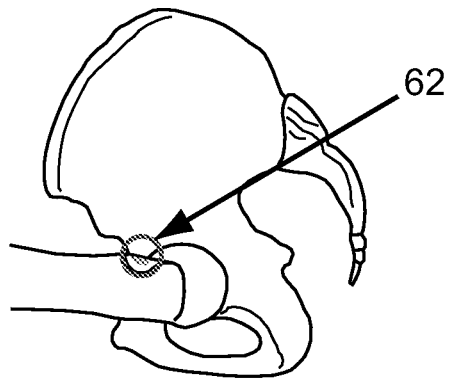
Fig. 6A                     Fig. 6B
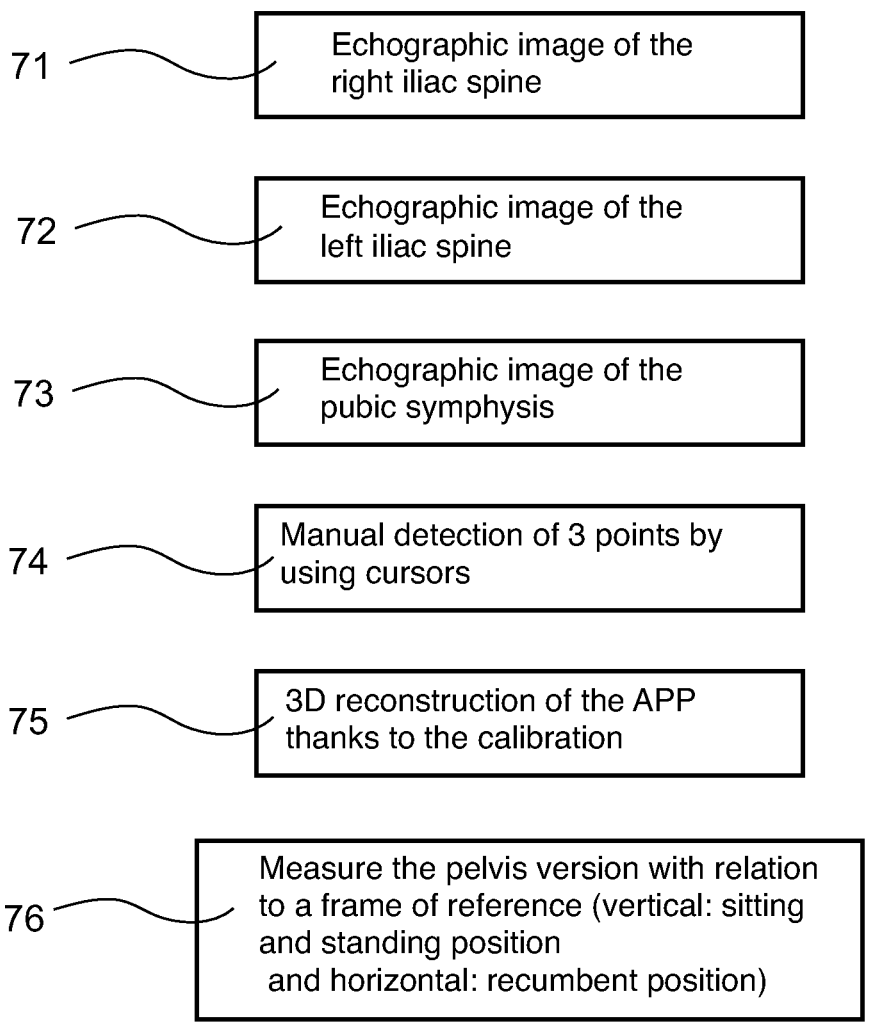
Fig. 7

HELP SYSTEM FOR IMPLANTING A HIP PROSTHESIS ON AN INDIVIDUAL

CROSS-REFERENCE TO RELATED APPLICATIONS

The present application is based on and claims the benefit of U.S. Provisional Patent Application No. 61/074,328, filed Jun. 20, 2008, the content of which is hereby incorporated by reference in its entirety.

STATEMENT REGARDING FEDERALLY SPONSORED RESEARCH OR DEVELOPMENT

None.

THE NAMES OF PARTIES TO A JOINT RESEARCH AGREEMENT

None.

FIELD OF THE DISCLOSURE

The field of the disclosure is that of implanting total hip prostheses. More precisely, the disclosure relates to a computerized system enabling optimized placement of the constituent elements of such a prosthesis on an individual.

BACKGROUND OF THE DISCLOSURE

A total hip prosthesis generally includes two parts: a first part integrally connected to the femur, known as the femoral part comprising a rod introduced in the femur, equipped with an essentially spherical head, and an acetabulum provided to receive the femoral head. The acetabulum, also known as a cup when it is hemispherical, is positioned in the corresponding housing (the anatomical acetabulum) of the hip bone.

Implantation of a prosthesis by a surgeon is a relatively complex operation, since the femoral part and the acetabulum even more so, must be placed in an optimized manner, particularly to prevent the prosthesis from dislocating during high amplitude movements.

According to conventional methods, the pelvis is palpated to locate the three points of the anterior pelvic plane (APP). This anterior pelvic plane (also known as the Lewinneck plane) is a frame of reference conventionally utilized in hip surgery. It is defined by the two iliac spines and by the pubic symphysis. This plane enables the prosthetic acetabulum to be adequately oriented in terms of inclination and anteversion.

The surgeon then inserts the acetabulum or cup at the end of a tool known as an impactor. He manipulates this cup so as to place it such that it presents an inclination of 45° and an anteversion of 15° with relation to the anterior pelvic plane.

However, these two angle values are average values, utilized by default, and do not correspond to all particular positions likely to be encountered.

An improvement to this approach was proposed in the document of patent U.S. Pat. No. 6,205,411, that proposes a computerized simulation of an optimized prosthesis implantation from a tomography of the bone envelope of the pelvis and femur, done before the operation.

During the operation, the surgeon is guided in placing the acetabulum, by using an inner body placed on the pelvis and the femur to ensure location in space, according to the simulation result.

This result is effective but presents the disadvantage of significant complexity (tomography, computerized simulation, etc.) that limits its use, particularly for reasons of cost.

Another approach was proposed in the document of patent FR-2 865 928. According to this technique, a "mega-head" is used, placed in the cotyloid cavity hollowed in the pelvis. A processing device enables a mobility cone and extreme positions to be simultaneously displayed, according the center of the cup and the geometry of the femoral prosthesis.

The surgeon may then manipulate the cup by using an impactor to bring the extreme positions into the mobility cone.

This technique is more simple than that described in document U.S. Pat. No. 6,205,411, and does not necessitate prior measurements. However, this technique may turn out to be insufficient in practice, since the measurements are performed during surgery, and the individual is put to sleep in a particular position (recumbent position).

SUMMARY

An aspect of the disclosure relates to a help system for implanting a hip prosthesis in an individual, comprising an acetabulum intended to be placed in the hip bone of said patient and a femoral part intended to be integrally connected to the femur of said individual.

According to an example embodiment, such a system comprises:
  means for imaging the human body, comprising means for locating the position of images in space;
  means for calculating the pelvis version of said individual in at least three reference positions, respectively standing, recumbent and sitting, by analyzing the images issued by said imaging means;
  means for measuring the position of said acetabulum with relation to the pelvis of said individual;
  means for simultaneously restoring representative information from the prosthetic mobility of the hip with relation to each of said reference positions, for a standard position of said acetabulum.

Thus, an aspect of the disclosure is based on a new and inventive approach that takes several reference positions into account so as to optimize the placement of the total hip prosthesis, to reduce the risks of dislocation and to restore proper leg length.

In one particular embodiment, said means for determining the pelvis version comprise, for each reference position:
  means for analyzing at least three images, including:
    a first image of an upper right zone of the hip bone of said individual;
    a second image of an upper left zone of said hip bone;
    a third image of a lower zone of said hip bone;
  means for identifying the characteristic points, that is, on said first image a point corresponding to the position of the right iliac spine, on said second image a point corresponding to the position of the left iliac spine and on said third image a point corresponding to the position of the pubic symphysis;
  means for determining an anterior pelvic plane from said three points, introduced in a three-dimensional frame of reference associated with said locating means;
  means for evaluating the pelvis version with relation to a reference direction, according to said anterior pelvic plane.

Advantageously, said restoring means comprise means for displaying an impingement circle for each reference position, and the corresponding neutral position.

By consulting the different circles, the practitioner may retain the position of the prosthesis corresponding to the best compromise, while, according to known techniques, he would optimize this position for only the recumbent position, which may lead to aberrations in other positions.

According to a preferential embodiment, said display means also issue maximum angle values for a set of possible movements, for each reference position.

Said possible movements may in particular belong to the group comprising extension, flexion, rotations, abduction and adduction.

According to an advantageous embodiment, said imaging means may comprise an ultrasound echography probe equipped with a rigid locating body visible by a navigation station.

This station locates these rigid bodies by infrared radiation. The ultrasound probe is calibrated with relation to the optical localizer.

The system, in one aspect of the disclosure, may also comprise means for determining the position of at least three summits of the anatomical acetabulum of said individual, and means for correcting said impingement circles, so as to take anatomical impingements into consideration.

In fact, the inventors have detected that prosthetic impingement circles are sometimes inaccurate, and include positions that are anatomically not acceptable. An aspect of the disclosure thus proposes correcting these circles, to issue anatomical impingement circles, so as to further reduce the risks of poor prosthesis placement, and thus dislocation.

According to an advantageous embodiment, said correction means take a collision circle determined thanks to said three summits.

The measurements and calculations are thus relatively simple and fast.

Advantageously, a system according to the an exemplary aspect of the disclosure also comprises means for determining the geometry of the femur of said individual, issuing at least one piece of information representative of the position of the inferior epicondyles and at least one piece of information representative of the position of the neck and head of the femoral prosthesis.

Said means for determining the geometry of the femur may particularly comprise position markers intended to be integrally connected to said femur.

These determination means may for example comprise palpation means.

The disclosure also relates to a help process for implanting a hip prosthesis in an individual, comprising an acetabulum intended to be placed in the hip bone of said patient and a femoral part intended to be integrally connected to the femur of said individual.

Such a method comprises, according to an exemplary aspect of the disclosure, the following steps:
 obtaining, before the operation, images issued by the human body imaging means, comprising means for locating the position of images in space, said images being taken in at least three reference positions, respectively standing, recumbent and sitting;
 determining, before the operation, the pelvis version of said individual in different positions by analyzing said images;
 measuring, during the operation, the position of said acetabulum with relation to the pelvis of said individual;
 simultaneously restoring, during the operation, information representative of the prosthetic mobility of the hip with relation to each of said reference positions, for a standard position of said acetabulum.

An aspect of the disclosure also relates to a data support containing a computer program executable by a microprocessor, characterized in that the program comprises program code instructions for the execution of the steps of the method above, when it is executed on a computer.

An aspect of the disclosure also relates to a method of implanting a total hip prosthesis in a patient, comprising the steps of:
 determining, before the operation, the pelvis version with relation to a reference direction of said patient for at least three reference positions by using a system such as described above;
 implanting a femoral prosthesis in the medullary canal of a femur to obtain a femur equipped with a femoral prosthesis;
 measuring the predetermined geometric dimensions of said femur equipped with a femoral prosthesis;
 determining the mechanical axis of said femur equipped with a femoral prosthesis from said measured dimensions;
 placing the prosthetic acetabulum in the hip bone;
 positioning said prosthetic acetabulum by using a system such as described above.

BRIEF DESCRIPTION OF THE DRAWINGS

Other characteristics and advantages will appear more clearly upon reading the following description of an embodiment of the disclosure, given by way of a simple illustrative, non-limiting example, and the attached drawings among which:

FIGS. 2A to 2C show the position of the pelvic plane with relation to a reference plane, respectively in:
 FIG. 2A: standing position;
 FIG. 2B: recumbent position;
 FIG. 2C: sitting position;

FIG. 3 illustrates an example of an angle of functional anteversion;

FIG. 4 illustrates an example of an angle of functional inclination;

FIGS. 5A to 5C show the variations in orientation of the acetabulum according to the position of the pelvis;

FIGS. 6A and 6B respectively illustrate a posterior conflict between the acetabulum and the femur in standing position and an anterior conflict between the acetabulum and the femur in sitting position;

FIG. 7 is a simplified flow chart of the implementation of the system according to an illustrative aspect of the disclosure, for determining the pelvic plane;

DETAILED DESCRIPTION OF ILLUSTRATIVE EMBODIMENTS

1. Introduction

The inventors of the present disclosure have observed that an implantation under the conditions described above in the Background section is often not optimal, since it only takes this particular position, the recumbent position, into account, and not other possible positions, in particular standing and sitting positions.

However, it appears that an optimal position in the recumbent position may not be optimal in the sitting or standing position.

In other words, collisions between the prosthesis and the acetabulum may be produced, likely to lead to a dislocation, in certain situations, even when the acetabulum was placed optimally with relation to the anterior pelvic plane determined in the recumbent position.

One of the main constraints for positioning a total hip prosthesis is thus to optimize the position and orientation of the implant, in order to prevent postoperative instabilities. To do this, a frame of reference, known as the Lewinneck plane or anterior pelvic plane defined by the two iliac spines and by the pubic symphysis, is used in computer-assisted hip surgery.

It is apparent that this frame of reference varies, sometimes significantly, during daily activities and from one patient to another, and may lead to postoperative instabilities.

In order to prevent any problems, an aspect of the disclosure is based on new means allowing a new procedure to be implemented, taking the pelvic behavior under different positions into consideration for placing a total hip prosthesis. This allows the prosthetic mobility of the hip in these different positions to be estimated.

2. Exemplary Embodiments

Figure 1:
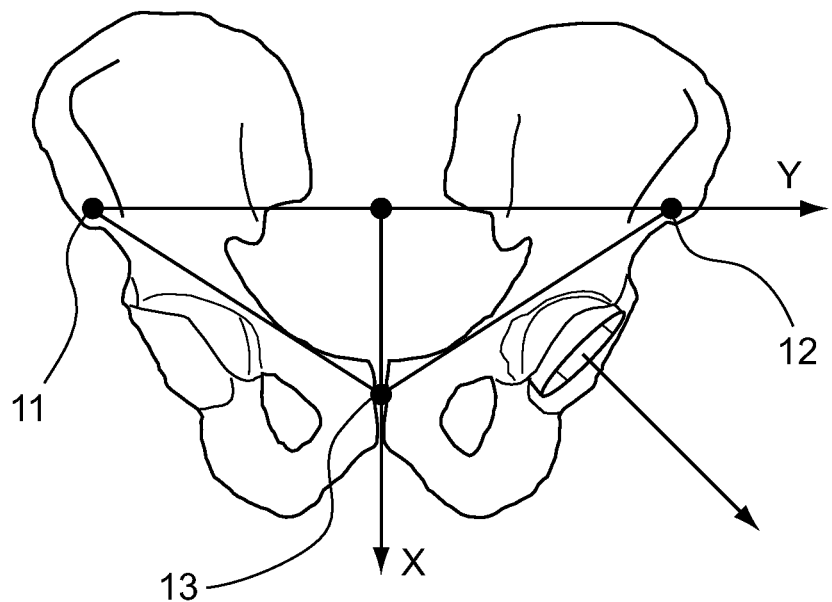
FIG. 1 illustrates an anterior pelvic plane and its three characteristic points.

FIG. 1 presents the pelvic plane (xy) defined by the points corresponding to the two iliac spines 11 and 12 and the pubic symphysis 13 on the hip bone 14. The prosthetic acetabulum 4 must be adequately oriented, in terms of inclination and anteversion.

Figures 2A, 2B, 2C:
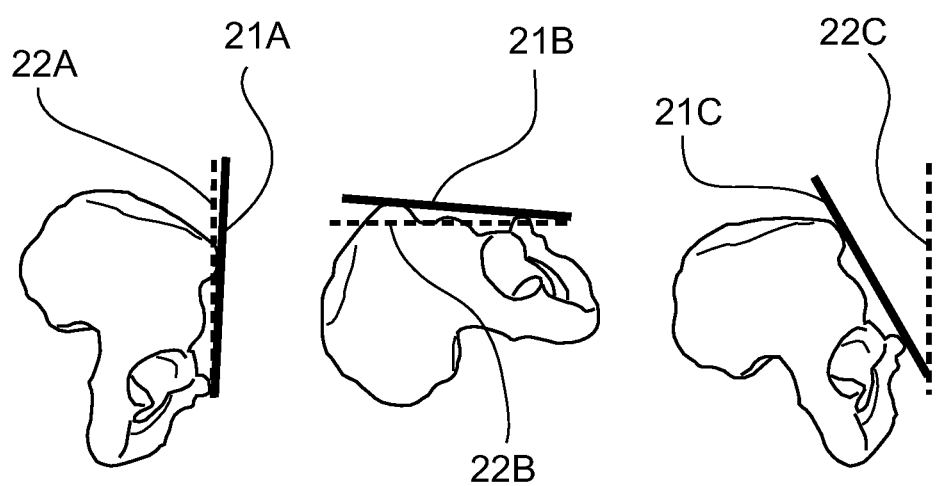

As seen in FIGS. 2A, 2B and 2C, the pelvic plane $21_A$, $21_B$, $21_C$ may vary with relation to a vertical or horizontal reference plane $22_A$, $22_B$ and $22_C$.

This dynamic behavior of the pelvis introduces modifications concerning the functional orientation of the acetabulum. The functional orientation, functional anteversion and functional inclination are calculated with relation to a fixed frame of reference, the vertical frontal plane, to study the dynamic behavior of the acetabulum in these different positions.

FIG. 3 illustrates the angle of functional anteversion 31 and FIG. 4 illustrates the angle of functional inclination 41.

In FIGS. 5A to 5C, it is observed that the orientation of the acetabulum 51, represented by the normal vector 52, varies according to the position of the pelvis:

FIG. 5B: standing position;

FIG. 5C: sitting position.

FIG. 5A illustrates the pelvis with relation to a vertical reference plane 53.

In the sitting position, the functional anteversion and inclination are greater than the functional anteversion and inclination in the standing position. This allows the acetabulum to be non-overlapping to promote flexion of the hip. However, collisions may appear in certain positions, despite a prosthetic acetabulum adequately oriented during surgery in a position of rest.

This is due to the influence of pelvic dynamics on the functional orientation, as illustrated by FIGS. 6A and 6B that respectively illustrate:

FIG. 6A: a posterior conflict 61 between the acetabulum and the femur in standing position;

FIG. 6B: an anterior conflict 62 between the acetabulum and the femur in the sitting position.

An exemplary embodiment of the disclosure takes these pelvic dynamics into consideration when placing a total hip prosthesis, to prevent such conflicts.

To do this, according to a particular embodiment of the disclosure, a procedure based on a calibrated 2.5 D echography system coupled to a navigation system is implemented.

This approach presents the advantage of preventing any radiation and of being simple, fast and precise.

The system comprises echography means, by the use of which the two iliac spines and the pubic symphysis may be scanned. A cursor is then placed, by means of a computer, on the three images representing these reference points.

The system then delivers a representation of the anterior pelvic plane in three dimensions, thanks to the calibration that was performed beforehand on the ultrasound probe. Lastly, the pelvis version is measured between the anterior pelvic plane and a frame of reference (vertical or horizontal according to the positions).

This is summarized in the flow chart from FIG. 7: an echographic image of the right iliac spine (71) then the left iliac spine (72) and lastly the pubic symphysis (73) are obtained.

These three points are then located by using cursors (74), and then the anterior pelvic plane is reconstructed in three dimensions (75) thanks to the calibration. Lastly, the pelvis version is measured (76) with relation to the frame of reference (vertical for sitting and standing positions, and horizontal for the recumbent position).

Of course, other imaging modalities may be used to measure tilting of the pelvis, such as the EOS (registered trademark) system, developed by the Biospace (registered trademark) company, or x-rays in two profile dimensions.

Figure 8:
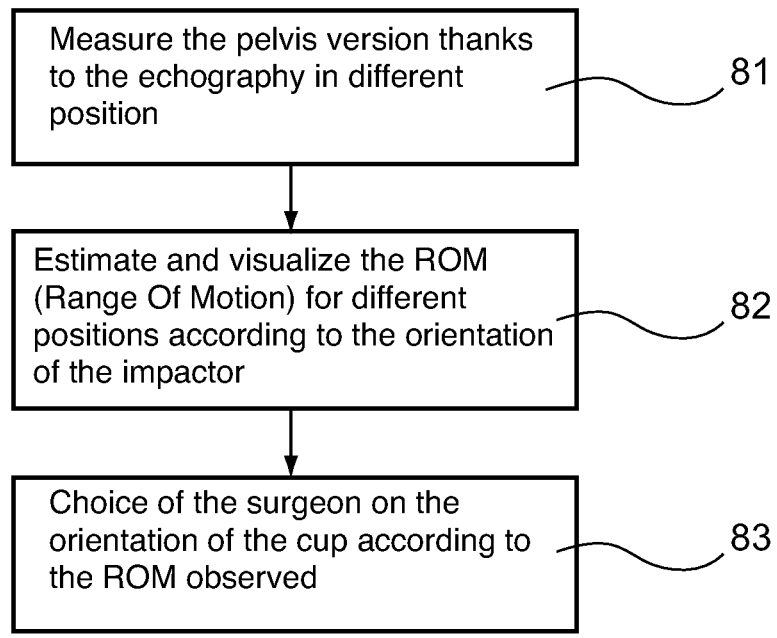
FIG. 8 is a simplified flow chart of the utilization of the system of an aspect of the disclosure, before the operation and then during the operation.

Thanks to this information, the protocol for placing a total hip prosthesis may be that illustrated in FIG. 8, that is:

before the surgery: measuring the pelvis version thanks to the echography in different situations or positions (81);

during the operation:

estimating and visualizing the range of motion or ROM for different positions according to the orientation of the impactor (82);

choice of the surgeon on the orientation of the cup according to the observed ROM (83).

Figure 9:
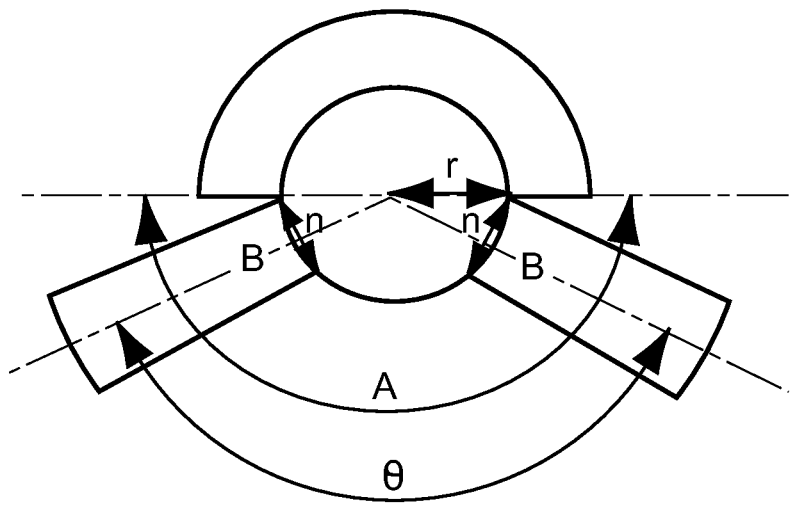
FIG. 9 illustrates the data for calculating a mobility cone.

Estimating the prosthetic mobility is based on determining the mobility cone. This is obtained thanks to the geometry of the prosthesis, and finds expression in, with reference to FIG. 9, the following equation:

$$\theta = A - 2\sin^{-1}\left(\frac{n/2}{r}\right)$$

Where: A is the angle of opening of the prosthetic acetabulum;

N is the diameter of the femoral prosthesis neck; and

R is the radius of the cup.

Figure 10:
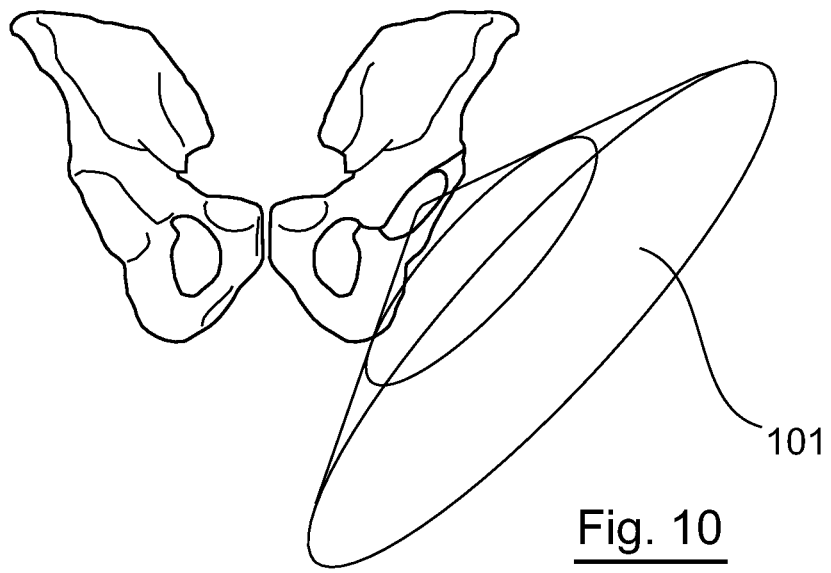
FIG. 10 illustrates a mobility cone associated with an acetabulum.

As illustrated in FIG. 10, this mobility cone 101 represents the maximum variation that the femoral head may carry out without prosthetic collision between the acetabulum and the femoral neck. In order to evaluate the prosthetic mobility of the hip, this mobility cone is placed and oriented according to the position of the prosthetic acetabulum.

Figure 11:
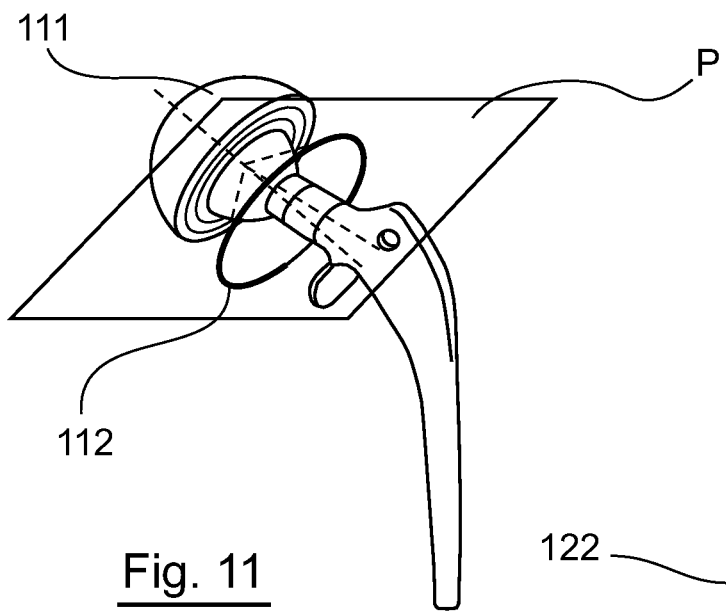
FIG. 11 illustrates the determination of an instability circle.

To visualize the position of the femoral neck with relation to the collision limit or impingement, a two-dimensional analysis is carried out. To do this, as illustrated in FIG. 11, a plane P is placed at an arbitrary normal distance to the cup 111.

Figure 12:
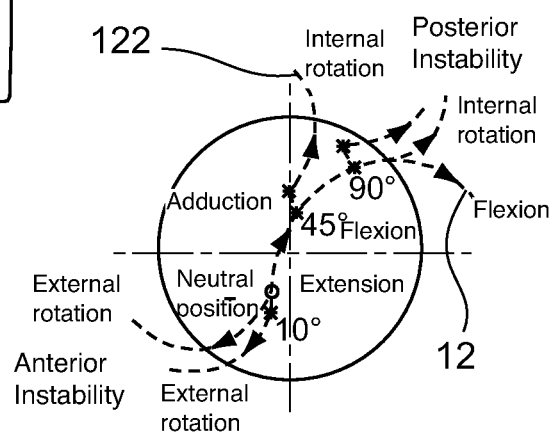
FIG. 12 presents the instability circle obtained according to the technique from FIG. 11.

The intersection line of this plane with the mobility cone defines an instability circle 112, an example of which is illustrated in FIG. 12.

The position of the femoral neck with relation to this instability circle is the intersection between this plane and the guideline of the femoral neck. It is then possible to determine lines 121, 122, etc., representing movements performed by the femur. This is useful for simulating movement. Nevertheless, to know the values of these different maximum movements (flexion, extension, abduction, adduction, internal rotation, external rotation) it is necessary to obtain a neutral position from which all these values will be calculated.

The neutral position is thus known when the mechanical axis of the femur is placed vertically with the axis of the condyles parallel to the Lewinneck plane. All the values of these different maximum movements are thus calculated from this initial position.

Figures 13A, 13B:
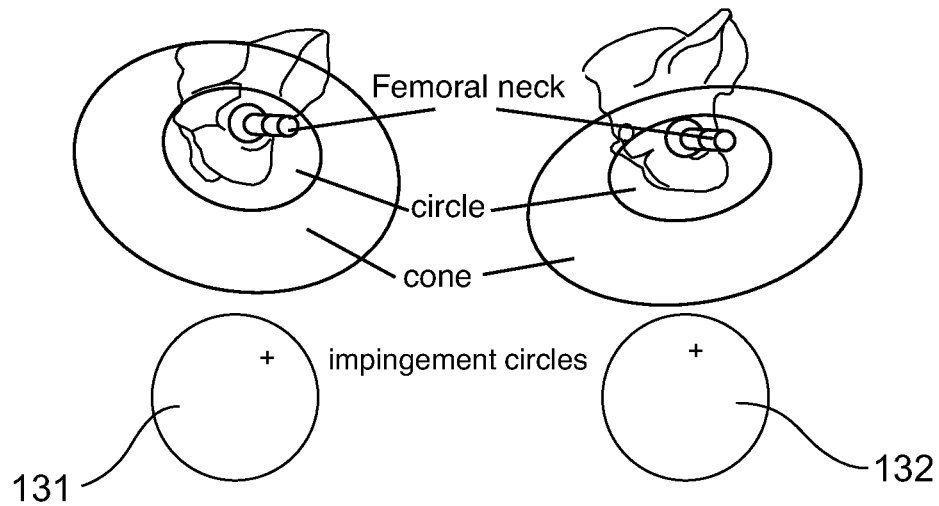
FIG. 13 illustrates, respectively in the sitting position and in the vertical position, the neutral position of the femur on the impingement circle.

As illustrated by FIG. 13 corresponding respectively to the seated position and to the vertical position, it is observed that according to the value of the pelvis version, the neutral position of the femur changes on the impingement circle 131, 132.

A method for calculating mobility angles is presented in further detail in the appendix.

Thus, the maximum values of the different movements are not the same according to the positions. It is for this reason that, according to an exemplary embodiment, these different positions are restored simultaneously, to enable the practitioners to identify the optimal compromise.

The practitioner, having determined during the operation the position of the Lewinneck plane with relation to the pelvis frame of reference by using the system from an exemplary embodiment of the disclosure, will place the femoral prosthesis in the medullary canal and then determine during the operation, still by using the system from the present disclosure, the geometry of the femur with relation to the femur frame of reference. In particular, he determines the connection between the head and the neck and the orientation of the femoral neck.

He then determines the mechanical axis of the femur with relation to the femur frame of reference, by determining the center of the femoral head and the center of the knee.

He then integrates the values of the pelvis version studied during the operation in the system from an embodiment of the disclosure, and then displaces, by using an impactor, the cup with relation to the Lewinneck plane. According to the displacement of this cup, the system from an embodiment of the disclosure estimates, in real time, the neutral position on the three impingement circles representing the three tilt positions of the pelvis measured (seated, standing).

Figure 14:
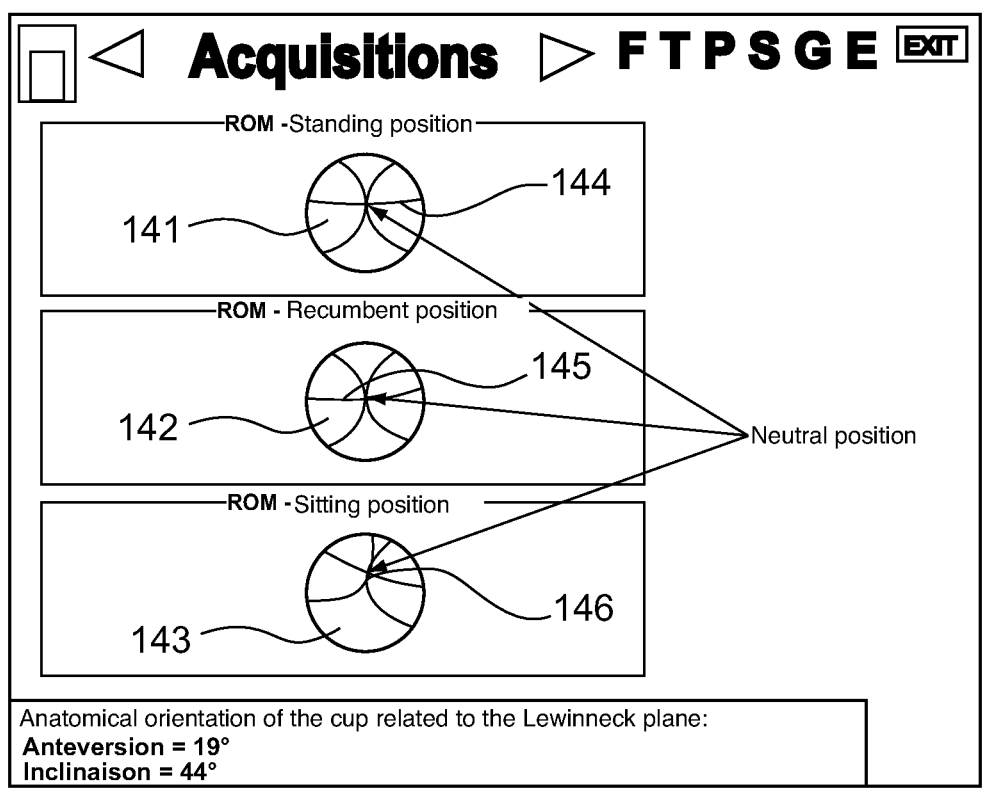
FIG. 14 presents an example of display on a screen of several impingement circles.

As illustrated in FIG. 14, that presents an example of a display on a screen, the system from an embodiment of the disclosure then displays (on one or more screens) impingement circles 141, 142 and 143 and the maximum values for the different extension movements (flexion, rotations, abduction and adduction) for each position.

As seen in this FIG. 14, the neutral positions 144, 145 and 146 vary according to the different positions, and thus according to the values of the corresponding pelvic version. The values of the maximum movements are thus also different.

The practitioners then search, by successive tests by displacing the impactor, for the position of the prosthetic acetabulum that optimizes these different values.

Pelvic behavior has a considerable influence on the orientation of the acetabulum to promote movements of the hip in certain daily positions (sitting, standing, recumbent). It is thus beneficial, according to an advantageous embodiment of the disclosure, to take these dynamics into consideration during placement of a total hip prosthesis (THP) in order to avoid any postoperative instability.

In fact, the system described above enables the THP to be positioned according to these dynamics and is based particularly on two means ensuring:

measuring pelvic behavior before the operation according to a method based on 2.5 D echography;

aiding the decision of the surgeon during the operation to take these dynamics into consideration thanks to an application developed on the navigation station.

One disadvantage of this technique is that only the prosthetic impingement is taken into consideration. An improvement, allowing bone impingements to also be integrated, is presented below.

According to the previous approach, prosthetic impingement is obtained thanks to obtaining the mobility cone associated with the prosthesis. A 2D visualization is also possible (impingement circle).

An embodiment of the disclosure provides, for this variation, means for palpating the acetabulum, allowing the anatomical impingement to be determined. Several approaches may be possible, but the use of a simple and fast procedure is desirable in the operating theatre.

Figure 15:
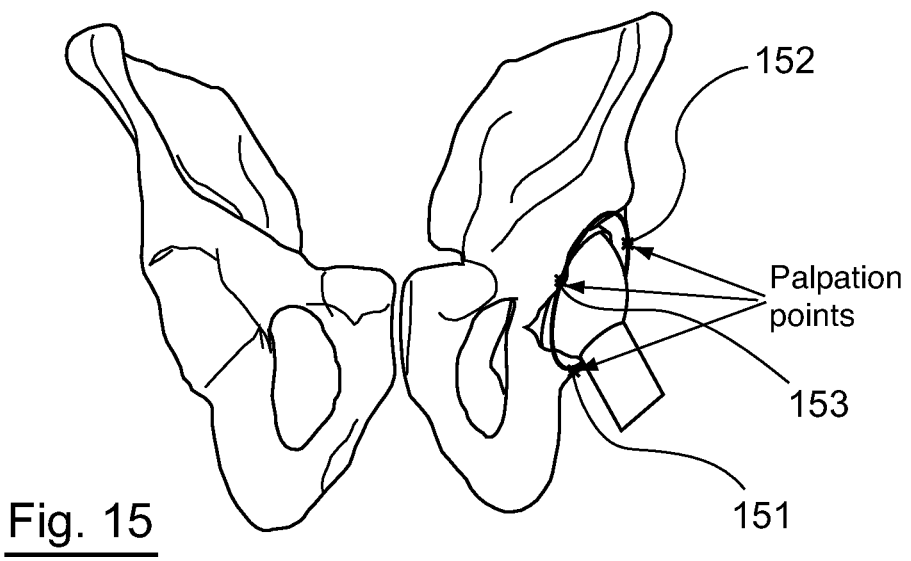
FIG. 15 illustrates the delimitation of the anatomical acetabulum by using the three characteristic points.

A first implementation considered is to palpate the entire delimitation of the acetabulum. Nevertheless, this method is difficult to carry out and is very sensitive at poorly palpated points. Preferentially, the palpation means thus enable the position and orientation of the acetabulum limit to be approximated by a circle by only taking three points 151, 152 and 153 into account, as illustrated in FIG. 15.

These three points are chosen cautiously in order to not erroneously delimit the acetabulum. The idea is thus to choose the points that produce the result with the most limited anatomical mobility. In fact, it is better to give lower mobility results than real results to be sure that there would not be any impingement. The three points thus will be those situated on the highest bone "summits."

Figure 16:
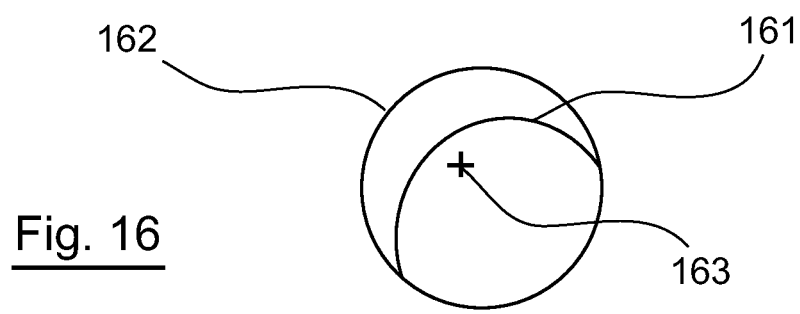
FIG. 16 illustrates the taking into consideration of the bone limit of the acetabulum, on an impingement circle.
Figure 17:
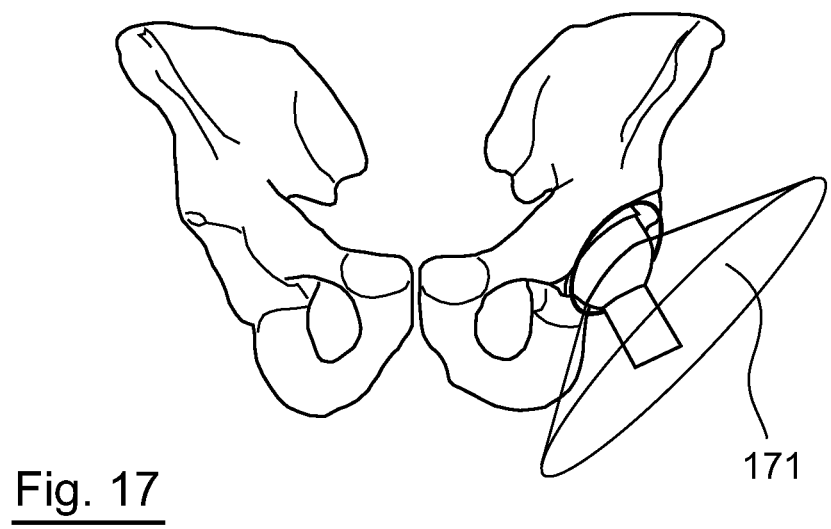
FIG. 17 shows the cone representing the prosthetic mobility obtained by considering the impingement circle of FIG. 16.

A circle 161 is then adjusted at these three points to obtain the bone limit of the acetabulum, as illustrated in FIG. 16. A cone representing the prosthetic mobility is then obtained (FIG. 17). The summit of this cone is the position of the femoral head 163 and passes by the circle defined by the three points. This method then enables the prosthetic impingement circle 162 to be limited in order to take anatomical impingements into consideration.

The mobility of the hip may thus be limited not only by the prosthesis, but also by the anatomy itself. The system from an exemplary embodiment of the disclosure enables the anatomical impingement to be taken into consideration, and consequently enables aberrations in calculating the mobility of the hip (flexion, extension, abduction, adduction, internal rotation and external rotation) to be prevented.

Implementation of the system or device described above will be summarized below.

First, means for measuring before the operation, comprising an ultrasound probe to which is fixed a rigid body to enable its position with relation to the posture to be located, issue a series of measurements. Previously, the "shot" distance with relation to the probe was calibrated, for example according to the technique explained in document FR 07 08476.

The following operations are performed before the operation:
a) placing a rigid body in the pelvis;
b) dislocation of the femur;
c) placing a rigid body on the femur;
d) palpating the three points of the Lewinneck plane (locating in space) to locate this plane in space;
e) measuring the geometry of the femur (palpating the rigid body and condyles, as well as the neck and head of the femoral prosthesis);
f) inserting the cup at the end of the impactor (handling arm with markers to locate its position);
g) manipulating the impactor and, in real time (step g1): displaying the mobility angle values on a screen;
g1) the treatment phase is broken down as follows:
  resetting (3 rotations+1 translation) the femur in a neutral position for the current pelvis position/neutral position ((i) the head of the femoral prosthesis is in place in the cup, (ii) the axis of the condyles is parallel to the Lewinneck plane (iii) the mechanical axis of the femur is parallel to the reference axis);
  determining the maximum flexion/extension, internal rotation/external rotation and abduction/adduction angles by simulating the rotation of the mechanical axis of the femur around an axis:
    (i) passing by the two iliac spines,
    (ii) coincident with the "vertical" axis,
    (iii) vector product of the 2 previous axes,
    to identify the angle (maximum angle) for which the guiding axis of the femoral neck (part of the prosthesis) cuts the collision circle (also known as impingement circle, intersection of the mobility cone with an arbitrary plane perpendicular to the central axis of the cup);
  rotating the pelvis, to place it in a second position (sitting, standing) where the Lewinneck plane presents an orientation known from the preoperative phase with relation to the reference direction. The femur remains immobile. Again, determination of the neutral position (intersection of the axis of the femoral neck with the plane of the impingement circle), and maximum angles following the method described in g1);
  restoring the maximum angles and the impingement circle on a screen for each of the three positions;
h) when the values displayed are satisfactory to the surgeon (the cup is correctly positioned), the impactor is removed from the cup.

3. Appendix

Calculating Hip Mobility Angles

To visualize the position of the femoral neck with relation to the collision limit (or impingement), 2D analysis is used. To do this, a plane (P) is placed at a normal arbitrary distance to the cup (FIGS. 12 and 13). The intersection of this plane with the mobility cone defines an instability circle. The position of the femoral neck with relation to this instability circle is the intersection between this plane and the guide line of the femoral neck. It is then possible to determine the lines on this circle representing the movements performed by the femur (FIG. 12) (useful for simulating movement).

Nevertheless, to know the values of these different maximum movements (flexion, extension, abduction, adduction, internal rotation, external rotation), it is necessary to obtain a neutral position from which all these values will be calculated.

According to the embodiment described, the neutral position is determined by referring to the method proposed by several authors, who propose that these different movements are measured with relation to the vertical (FIGS. 19A to 19C).

The neutral position is thus known when the mechanical axis of the femur is placed vertically with the axis of the condyles parallel to the Lewinneck plane. All the values of these different maximum movements will thus be calculated from this initial position.

According to the value of the pelvis version, the neutral position of the femur will thus change on the impingement circle (FIGS. 14A and 14B).

Thus, the maximum values of the different movements (extension, flexion, rotations, abduction and adduction) will not be the same according to the positions and the surgeon will benefit from receiving these differences when placing the THP.

The mobility angles (maximum flexion, maximum extension, etc.) are then calculated in the following manner. The neutral position of the mechanical axis of the femur (vertical position with the axis of the epicondyles parallel to the Lewinneck plane) is known.

Figure 18C:
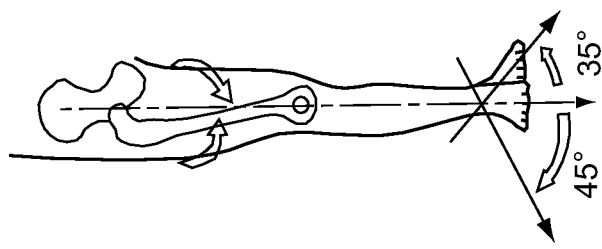
FIGS. 18A to 18C illustrate the different positions taken into consideration for determining the angles of mobility of the hip.
Figure 18B:
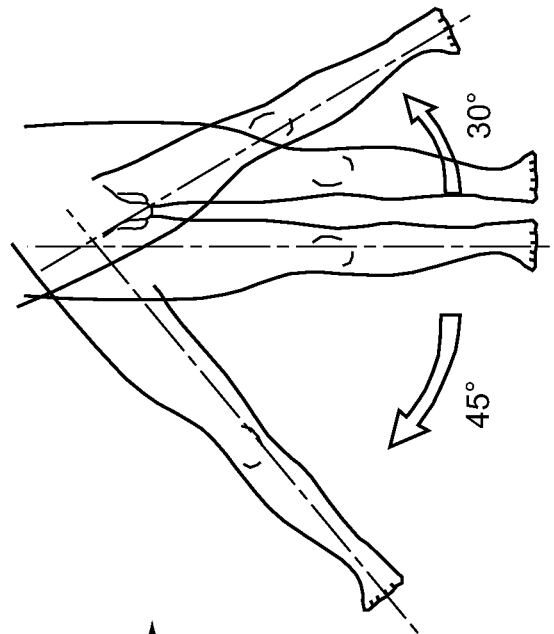
Figure 18A:
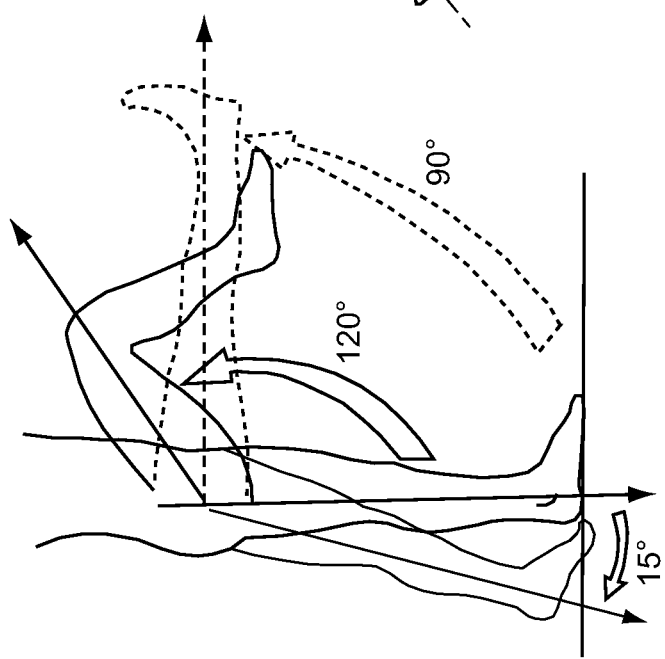

To calculate the angles, one only has to carry out the rotation (thanks to the application) of the mechanical axis of the femur according to the relevant axes (FIGS. 18A to 18C). When the position of the femoral neck on the 2D impingement circle is situated on the limit on the circle, the maximum angle before impingement is obtained.

To calculate the maximum flexion, one only has to carry out the rotation of the mechanical axis of the femur in front according to the axis defined by the two iliac spines of the pelvis. The maximum flexion is reached when the position of the femoral neck on the 2D impingement circle is situated on the circle. For the maximum extension, one only has to do the rotation according to the same axis at the rear.

To calculate the maximum internal rotation, one only has to carry out the rotation of the mechanical axis of the femur towards the inside according to the vertical axis. The maximum internal rotation is reached when the position of the femoral neck on the 2D impingement circle is situated on the circle. For the maximum external rotation, one only has to do the rotation according to the same axis towards the outside.

To calculate the maximum abduction, one only has to carry out the rotation of the mechanical axis of the femur towards the outside according to the axis defined by the vector product of the two previous axes. The maximum abduction is reached when the position of the femoral neck on the 2D impingement circle is situated on the circle. For the maximum adduction, one only has to do the rotation according to the same axis towards the inside.

To obtain the vertical, the pelvis is placed vertically (pelvis version=0°). The vertical is thus defined by the axis passing by the symphysis and the middle of the iliac spines. During the procedure, the position of the pelvis of the patient is known thanks to the posture. The geometry of the prosthesis that will be placed is also known. Lastly, the position and orientation of the femoral prosthesis in the femur as well as the mechanical axis of the femur are known.

The position and orientation of the prosthetic acetabulum is obtained thanks to the impactor.

The position of the pelvis obtained during the operation is our reference. Our "vertical" is thus obtained thanks to the symphysis and to the two iliac spines. The femoral prosthesis is positioned by computer (thanks to a resetting) inside the prosthetic acetabulum with an orientation of the mechanic axis identical to the "vertical" obtained thanks to the reference position.

Then all is relative to this reference position. According to the pelvis version measured before the operation, the pelvis is rotated according to the axis defined by the iliac spines. Thus, the angles are calculated in these different positions obtained thanks to the reference position.

4. Summary

An illustrative embodiment of the disclosure provides a help system or device when implanting a total hip prosthesis that limits the risks of dislocation, in different positions, and particularly in the recumbent, sitting and standing positions.

An illustrative embodiment provides such a system, that remains simple to implement, and that does not necessitate a complex data processing synthesis operation, in particular.

An illustrative embodiment provides such a system, taking the real physiological characteristics of the individual into consideration.

Although the present disclosure has been described with reference to one or more examples, workers skilled in the art will recognize that changes may be made in form and detail without departing from the scope of the disclosure and/or the appended claims.

What is claimed is:

1. A help system for implanting a hip prosthesis in an individual, the hip prosthesis having an acetabulum intended to be placed in the hip bone of said patient and a femoral part intended to be integrally connected to the femur of said individual, wherein the system comprises:
   means for imaging the human body, comprising means for locating position of images in space;
   means for calculating a pelvis version of said individual in at least three reference situations, respectively standing, recumbent and sitting, by analyzing images issued by said imaging means;
   means for measuring a position of said acetabulum of the hip prosthesis with relation to the pelvis of said individual;
   means for simultaneously restoring information representative of prosthetic mobility of the hip with relation to each of said at least three reference situations, for a current position of said acetabulum of the hip prosthesis, including means for displaying an impingement circle for each reference situation and a corresponding neutral position; and
   means for determining a position of at least three summits of an anatomical acetabulum of said individual, and means for correcting said information representative of the prosthetic mobility, so as to take anatomical impingements into consideration.

2. The system according to claim 1, wherein said means for determining the pelvis version comprise, for each reference situation:
   means for analyzing at least three images, including:
      a first image of an upper right zone of the hip bone of said individual;
      a second image of an upper left zone of said hip bone;
      a third image of a lower zone of said hip bone;
   means for identifying three characteristic points, comprising on each first image a point corresponding to a position of a right iliac spine, on said second image a point corresponding to a position of a left iliac spine and on said third image a point corresponding to a position of a pubic symphysis;
   means for determining an anterior pelvic plane from said three points, introduced in a three-dimensional frame of reference associated with said locating means;
   means for evaluating the pelvis version with relation to a reference direction according to said anterior pelvic plane.

3. The system according to claim 2, wherein said means for displaying also issue maximum angle values for a set of possible movements, for each reference position.

4. The system according to claim 3, wherein said possible movements belong to the group comprising extension, flexion, rotations, abduction and adduction.

5. The system according to claim 1, wherein said means for imaging comprise an ultrasound echography probe equipped with a rigid locating body visible by a navigation station.

6. The system according to claim 1, wherein said means for correcting take a collision circle determined thanks to said three summits.

7. The system according to claim 1, wherein the system comprises means for determining a geometry of the femur of said individual, issuing at least one piece of information representative of a position of an inferior epicondyles and at least one piece of information representative of a position of a neck and of a head of the femoral prosthesis.

8. The system according to claim 7, wherein said means for determining the geometry of the femur comprise position markers intended to be integrally connected to said femur.

9. The system according to claim 1, wherein said means for determining comprise palpation means.

10. A method for helping implant a hip prosthesis in an individual, the hip prosthesis having an acetabulum intended to be placed in the hip bone of said patient and a femoral part intended to be integrally connected to the femur of said individual during an operation, wherein the method comprises the following steps:
   obtaining, before the operation, images issued by means for imaging a human body, comprising means for locating a position of images in space, said images being taken in at least three reference situations, respectively standing, recumbent and sitting;
   determining, before the operation, a pelvis version of said individual in different positions by analyzing said images;
   measuring, during the operation, a position of said acetabulum of the hip prosthesis with relation to the pelvis of said individual;
   simultaneously restoring, during the operation, information representative of prosthetic mobility of the hip with relation to each of said at least three reference situations, for a current position of said acetabulum of the hip prosthesis, including displaying an impingement circle for each reference situation and a corresponding neutral position; and
   determining a position of at least three summits of an anatomical acetabulum of said individual, and correcting said information representative of the prosthetic mobility, so as to take anatomical impingements into consideration.

11. A non-transitory data support containing a computer program executable by a microprocessor, wherein the support comprises program code instructions for executing a method for helping implant a hip prosthesis in an individual, when the instructions are executed on a computer, wherein the hip prosthesis has an acetabulum intended to be placed in the hip bone of said patient and a femoral part intended to be integrally connected to the femur of said individual during an operation, and wherein the method comprises the following steps:

obtaining, before the operation, images issued by means for imaging a human body, comprising means for locating a position of images in space, said images being taken in at least three reference situations, respectively standing, recumbent and sitting;

determining, before the operation, a pelvis version of said individual in different situations by analyzing said images;

measuring, during the operation, a position of said acetabulum of the hip prosthesis with relation to the pelvis of said individual;

simultaneously restoring, during the operation, information representative of prosthetic mobility of the hip with relation to each of said at least three reference situations, for a current position of said acetabulum of the hip prosthesis, including displaying an impingement circle for each reference situation and a corresponding neutral position; and determining a position of at least three summits of an anatomical acetabulum of said individual, and correcting said information representative of the prosthetic mobility, so as to take anatomical impingements into consideration.

12. A method for implanting a total hip prosthesis in a patient during an operation, wherein the method comprises:

determining, before the operation, a pelvis version with relation to a reference direction of said patient for at least three reference situations, comprising:

generating images of the human body and locating a position of images in space;

calculating the pelvis version of said individual in at least the three reference situations, respectively standing, recumbent and sitting, by analyzing the images of the human body;

measuring a position of said acetabulum of the hip prosthesis with relation to a pelvis of said individual; and simultaneously restoring information representative of prosthetic mobility of the hip with relation to each of said at least three reference situations, for a current position of said acetabulum of the hip prosthesis;

determining a position of at least three summits of an anatomical acetabulum of said individual, and correcting said information representative of the prosthetic mobility, so as to take anatomical impingements into consideration;

implanting a femoral prosthesis in a medullary canal of a femur to obtain a femur equipped with a femoral prosthesis;

measuring predetermined geometric dimensions of said femur equipped with a femoral prosthesis;

determining a mechanical axis of said femur equipped with a femoral prosthesis from said measured dimensions;

placing a prosthetic acetabulum on the hip bone;

positioning said prosthetic acetabulum by using the system.

* * * * *